United States Patent [19]

Wojciechowski et al.

[11] Patent Number: 4,735,451
[45] Date of Patent: Apr. 5, 1988

[54] METHOD AND DEVICE FOR GRIPPING PARTS IN AN X-RAY INSPECTION SYSTEM

[75] Inventors: Charles R. Wojciechowski, West Chester; Theodore W. Sippel, Cincinnati; Douglas S. Steele; Joseph J. Sostarich, both of Fairfield, all of Ohio

[73] Assignee: General Electric Company, Cincinnati, Ohio

[21] Appl. No.: 832,982

[22] Filed: Feb. 25, 1986

[51] Int. Cl.⁴ .............................................. B66C 1/00
[52] U.S. Cl. .................................. 294/103.1; 414/729; 414/741; 414/723; 901/31; 901/39; 403/381; 269/254 CS; 269/234; 269/309
[58] Field of Search ................ 901/30, 31, 39, 36, 901/32, 33, 34, 35, 37, 38; 414/729, 732, 741, 686, 723, 607; 294/86.4, 88, 119.1, 103.1; 403/381, 353, 331, 13, 14; 269/254 CS, 234, 309, 310

[56] References Cited

U.S. PATENT DOCUMENTS

| | | | |
|---|---|---|---|
| 651,416 | 6/1900 | Elmstrom | 403/331 |
| 3,039,340 | 6/1962 | Livermont | 403/331 X |
| 3,371,953 | 3/1968 | Blatt | 901/37 X |
| 4,243,257 | 1/1981 | Shackleford | 294/103.1 X |
| 4,437,232 | 3/1984 | Araki et al. | 294/86.14 X |
| 4,473,249 | 9/1984 | Valentine et al. | 294/104 X |
| 4,507,045 | 3/1985 | Valentine et al. | 294/88 X |
| 4,607,873 | 8/1986 | Nusbaumer et al. | 294/88 |

FOREIGN PATENT DOCUMENTS

| | | |
|---|---|---|
| 3322142 | 12/1984 | Fed. Rep. of Germany . |
| 3410359 | 10/1985 | Fed. Rep. of Germany ...... 269/309 |
| 0200867 | 6/1983 | German Democratic Rep. . |
| 0108316 | 5/1964 | Netherlands . |
| 621572 | 8/1978 | U.S.S.R. . |
| 1141181 | 2/1985 | U.S.S.R. . |

Primary Examiner—Robert J. Spar
Assistant Examiner—Jennifer Doyle
Attorney, Agent, or Firm—Derek P. Lawrence

[57] ABSTRACT

A gripper for holding a manufactured part in a X-ray inspection system. The gripper includes a stationary jaw, a slidable jaw, a gripper base, a wear plate, a centering bushing an end plate, and a cam actuated spring mechanism for opening and closing the jaws. Both jaws are removable and adjustable in a keyway. Set screws are used to hold the jaws in place for a predetermined separation and allows a part to be positioned off center. The removable aspect allows for various jaw configurations. The centering bushing includes a cam shaped opening for accepting an end of an pneumatic activated ball plunger of a numerically controlled part manipulator. The centering bushing aligns the gripper to the longitudinal axis of the part manipulator.

3 Claims, 4 Drawing Sheets

METHOD AND DEVICE FOR GRIPPING PARTS IN AN X-RAY INSPECTION SYSTEM

BACKGROUND OF THE INVENTION

A. Field of the Invention

This invention generally relates to a mechanical gripper for holding a part, and more particularly, to a gripper for holding turbine blades on a conveyor system and in an X-ray inspection system.

B. Background Discussion

An X-ray inspection system for inspecting turbine blades includes a conveyor belt for transporting the blades from an operator loading station to an inspection station. The blades inspected are generally small in shape, typically less than 3 inches in diameter and less than 9 inches high. The manufacture of the blades has led to the development of blades containing complex interior passages and openings to the blade surface for blade cooling. An automated digital X-ray inspection system has been developed for the turbine blade inspection.

The X-ray inspection system is comprised of hardware for manipulating parts, generating X-rays, detecting X-rays, hardware for information transmission and computation, and software for controlling the software imaging system. Parts are carried into the X-ray machine by a multi-station conveyor. When the conveyor advances the blades to an inspection station, a numerically controlled part manipulator seizes the part and moves it to an inspection site between the X-ray beam and the X-ray detector. The X-ray inspection system then computes a digital fluoroscopy image while the part is moved vertically through the X-ray beam. In addition, a computed tomography image is generated with a part held in a constant vertical position and rotated through 360 degrees by the part manipulator. After imaging, the manipulator moves the part to the conveyor station and the conveyor station transports the part to an unload station for the operator.

It is an object of this invention to provide universal grippers which hold the turbine blade on the conveyor.

It is a further object of this invention to provide a gripper which can be mechanially connected to the part manipulator and moved up into the X-ray beam.

It is a further object of this invention to provide a gripper with an exact center of rotation aligned with the center of rotation of the part manipulator.

It is a further object of this invention to provide a gripper that fits in a pallet on the conveyor belt, but is easily seized by the part manipulator for transporting to the X-ray inspection site.

It is another object of this invention to provide a gripper for an X-ray inspection station with low attenuation material in the jaws.

SUMMARY OF THE INVENTION

The gripper includes a gripper body having a stationary jaw, a removable jaw, a gripper base, a wear plate, a centering bushing, an end plate, and a cam actuated spring mechanism for opening and closing the jaws. Each jaw fits into a keyway and is held firmly in the keyway by a set screw. A jaw may be positioned along the keyway by loosening the set screw. Since a jaw fits into a keyway, a jaw may be replaced with a jaw of a different design. The center bushing includes a cone shaped opening for accepting the end of a pneumatic activated ball plunger of a numerically controlled part manipulator. The wear plate of the gripper slides between the rigid arm portions of the part manipulator and the pneumatically actuated ball plunger is forced into the cone shaped shaft to center the gripper on the axis of rotation of the part manipulator. The wear plate of the gripper is forced against the part manipulator rigid arm portions to hold the gripper firmly in place during vertical and rotational motion of the part manipulator.

BRIEF DESCRIPTION OF THE DRAWINGS

FIG. 6 shows a top view of the slidable jaw assembly;

DETAILED DESCRIPTION OF THE ILLUSTRATIVE EMBODIMENT

A suitable X-ray inspection system for inspecting parts with X-rays is disclosed in U.S. Patent Application Ser. No. 832,511, titled X-ray Inspection System, filed concurrently herewith, assigned to General Electric Company. The disclosure which is hereby incorporated by reference. While the present invention is described hereinafter with particular reference to the X-ray inspection system, it is to be understood at the outset of the description which follows that it is contemplated that the device and methods in accordance with the present invention may be used with numerous manipulators for gripping various manufactured parts.

Figure 1:
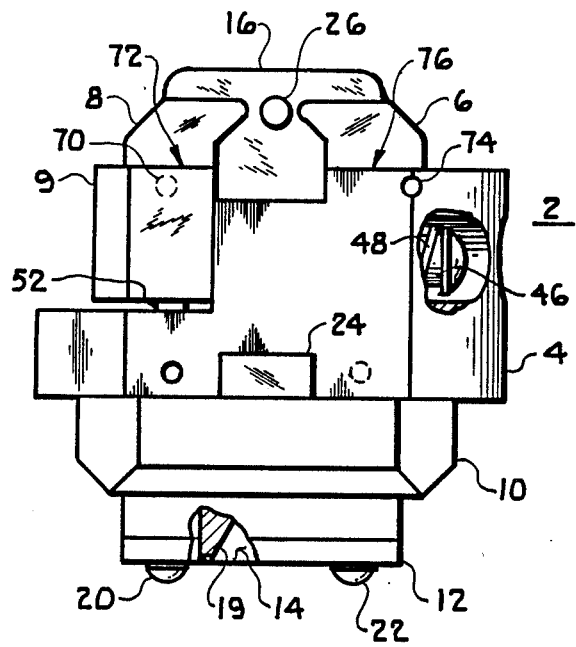
FIG. 1 shows a front view of the gripper assembly of the present invention.

FIG. 1 shows a front view of the gripper assembly 2 of the present invention. The gripper 2 includes a gripper body 4, a stationary jaw 6, a slidable jaw assembly 9, a gripper base 10, a wear plate 12, a center bushing 14 and an end plate 16. The gripper base 10 and wear plate 12 are held to the gripper body 4 by threaded members 20 and 22. The center bushing 14 includes a cone shaped opening 15 exactly centered along the center of the axis gripper.

The slidable jaw assembly 9 is attached to a pin 52 which moves in response to a movable cam 24. The movable cam 24 is pressed for compressing a spring mechanism 48 which moves the jaw 8 away from the stationary jaw 6. Releasing the cam 24 causes the compressed force of the spring mechanism 48 to force the jaws closed. A part is loaded into the gripper 2 between the movable jaw 8 and stationary jaw 6. The part is slid towards the end plate 16 until contact with an adjustment screw 26. The part is held firmly between the jaws while the gripper 2 and part are rotated and moved vertically. For a better understanding of the configuration and functional cooperation of the components described briefly above, attention is directed to FIG. 2–7 of the drawings, wherein the respective components are illustrated in detail.

Figure 2A:
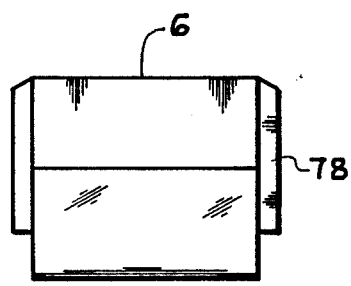
FIGS. 2A–C illustrates the removable jaws.
Figure 2B:
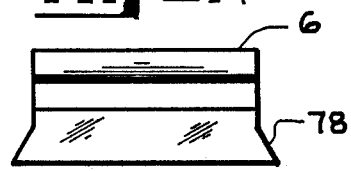
Figure 2C:
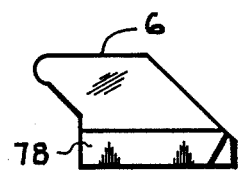
Figure 3A:
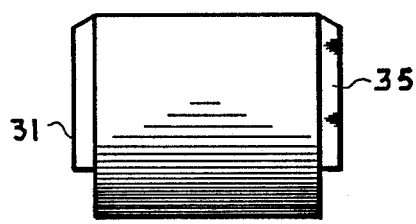
FIGS. 3A–C illustrates a different configuration for the jaws.
Figure 3B:
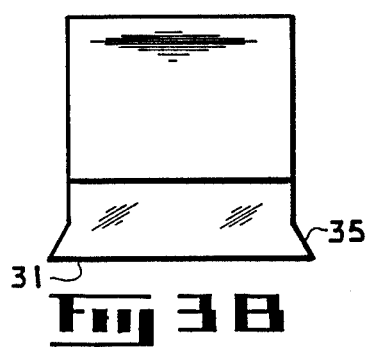
Figure 3C:
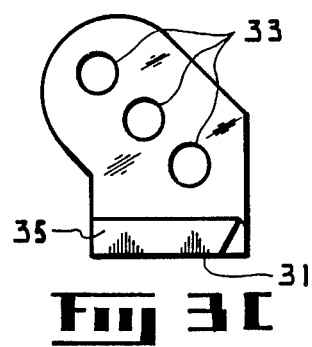

FIGS. 2A–C show the construction of jaw 6 and jaw 8. Each jaw has a chamferred portion 78. The chamferred portion 78 fits into a keyway in the gripper body and slidable jaw assembly 9. Referring briefly back to FIG. 1, jaw 8 fits into a keyway 72 and is held in position in keyway 72 by set screw 70. Similarly, set screw 74 holds jaw 6 into keyway 76. A jaw may be positioned on the keyway by loosening the set screw. Thus a predetermined separation is affected by positioning the jaws in the keyway. Also a part between the jaws can be positioned off center. The removable aspect allows for various jaw configurations to be used with the same gripper body, thereby allowing for the accomodation of a variety of parts. FIG. 3A–C show a different configuration jaw 31, the holes 33 in jaw 31 minimize X-ray attentuation. The jaw 31 has a chamferred portion 35 which fits into the gripper body keyways 72 and 76.

The jaws are made of material whose X-ray attenuation properties are low compared to those of the part inspected. Material such as aluminium is used. In using such material, the X-ray system is able to produce digital fluoroscopy and computed tomography images of the part material between the jaws, thereby allowing for whole part inspection capabilities. The jaws are anodized for wear.

Figure 4:
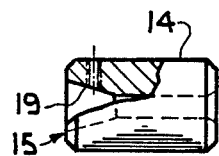
FIG. 4 is the centering bushing and center shaft.

FIG. 4 shows the centering bushing 14 and centering cone 19. The centering bushing 14 is firmly inserted into the gripper assembly 2 to form a secure nonslip fit. The centering bushing 14 includes an opening 15 and a centering cone 19. The center axis of the centering cone 19 corresponds to the center axis of the gripper assembly 2.

Figure 5:
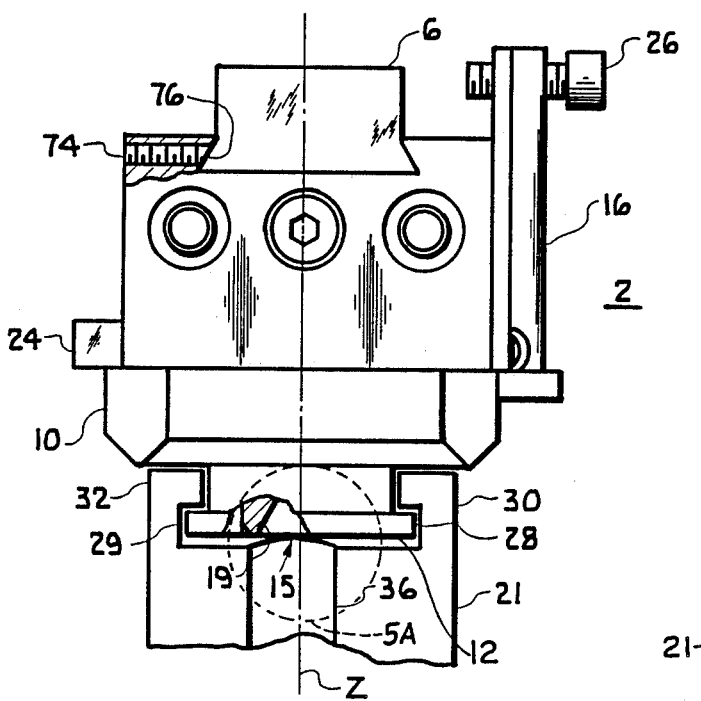
FIG. 5 illustrates a right side view of the gripper assembly.
Figure 5A:
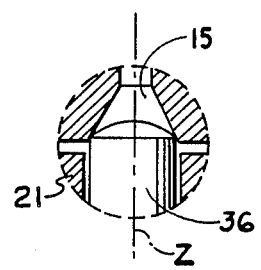
FIG. 5A is a cross-sectional view of area 5A of FIG. 5.

FIG. 5 shows the right side view of the gripper assembly 2. The end plate 16 includes a set screw 26 which adjusts the depth of a part inserted between the jaws. The stationary jaw 6 fits into keyway 76 and is held in position by set screw 74. The wear plate 8 extends beyond the gripper base 10 forming flanges 28 and 29. In operation, the wear plate 12 slides between rigid arm portions 30 and 32 of a part manipulator mandrel 21. The numerically controlled part manipulator responds to numerical controller commands to raise or lower the part manipulator mandrel 21 or rotate the mandrel 21 about the center axis Z. The part manipulator mandrel 21 includes a pneumatic controlled ball plunger 36. The ball plunger 36 moves longitudinally along the mandrel axis, on command from the numerical controller in a manner well known in the art. On command, the ball plunger 36 is forced into the centering bushing 14 for mating the ball plunger 36 with the conical surface 19 (see FIG. 5A). The interaction between the ball plunger 36 and the conical surface 19 forces the gripper assembly 2 to align on the center axis Z. The force exerted by the ball plunger 36 is counteracted by the force of the part manipulator rigid arm portions 30 and 32 against the wear plate 12 along the flange 28 and 29. The force exerted by the rigid arm portions 30 and 32 forms a friction force which firmly holds the gripper 2 in place. In addition the sides of the part manipulator rigid arm portions 30 and 32 prevent the gripper from shifting in the part manipulator mandrel 21. A movement in the mandrel 21 produces an exact resulting movement in the gripper 2. Thus as the ball plunger 36 is moved into the centering cone 19, the gripper self-aligns on the center axis and remains securely grasped by the part manipulator in response to the ball plunger's force.

FIG. 6 shows a top view of the slidable jaw assembly 9. The slidable jaw assembly 9 includes a slidable jaw 8, two alignment shafts 38 and 40, a spring shaft 46 and a spring 48. Alignment shaft 40 is inserted through a linear ball bearing unit 42 and alignment shaft 38 is inserted through linear ball bearing unit 44. The ball bearing units insert into cavities in the gripper assembly body allowing the slidable jaw 8 to move freely away from and towards the stationary jaw 6. The spring shaft 46 fits inside spring 48.

Figure 7:
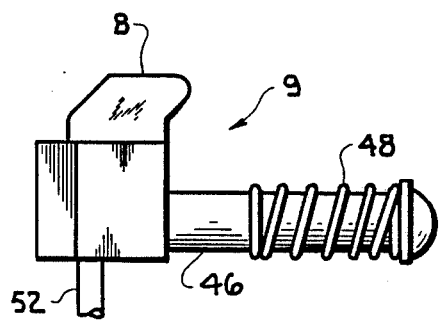
FIG. 7 illustrates a side view of the slidable jaw assembly.

FIG. 7 shows a side view of the slidable jaw assembly 9. The pin 52 is inserted into the slidable jaw assembly 9 perpendicular to the longitudinal axis of the spring shaft 46.

Figure 8A:
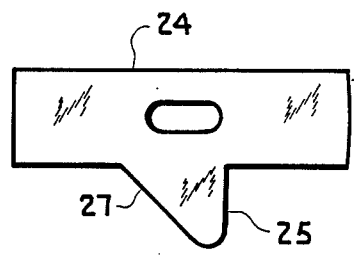
FIGS. 8A–B is the cam.
Figure 5:
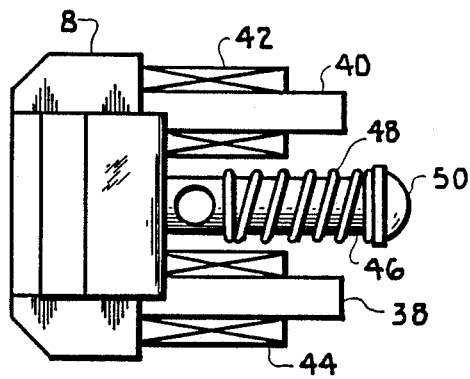
Figure 8B:

FIGS. 8A–B show the top and side view of the cam 24 respectively. The cam has a triangular portion 25 whose function will be discussed in reference to FIG. 7. The pin 52 of the slidable jaw assembly 9 contacts the cam surface 27 during operation of the gripper.

FIGS. 9A–E show the top, side, bottom, and end views of the gripper body. The cam 24 resides in slot 54. The pin 52 fits into slot 64. The slidable jaw assembly 9 fits into the three tunnels 56, 58, and 60. The stationary jaw fits into keyway 76.

It is important to note that tunnel 58 is composed of two portions 59 and 61. With the spring 48 removed, the slidable jaw assembly 9 is slid into three corresponding tunnels on the gripper body. The two outside tunnels 56 and 60 contain the linear ball bearing units 42 and 44. Tunnel 58 has a first portion 59 with a diameter just slightly larger than the spring shaft 46, but smaller than the spring 48 diameter. The first portion 59 opens into a second portion 61 of tunnel 58 with a diameter large enough for spring 48. The second portion 61 allows access to spring shaft 36 from the side of the gripper 2. The spring 48 is inserted onto spring shaft 46 and is forced against portion 59 of tunnel 58. A threaded member 50 is inserted into the spring shaft 46 for retaining spring 48 on shaft 36. Moving the slidable jaw 8 away from the gripper compresses the spring 48 against portion 59 and the threaded member 50. The compressable force of the spring 48 urges the slidable jaw towards the gripper 2 having the stationary jaw 6.

Figure 10:
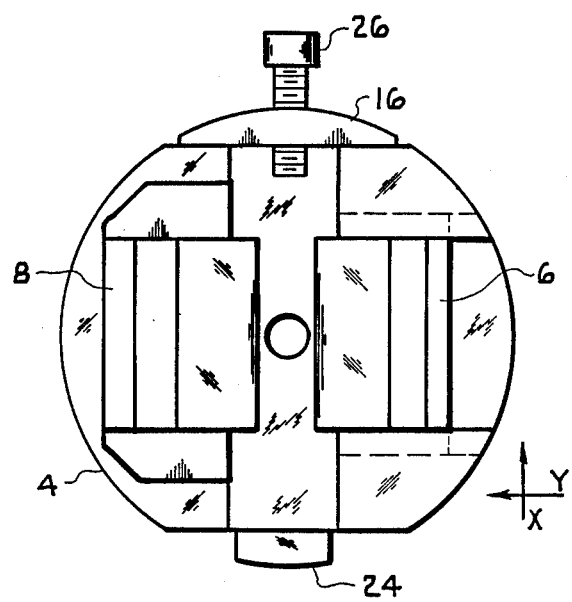
FIG. 10 shows a top view of the gripper assembly, illustrating the function of the cam assembly.
Figure 9A:
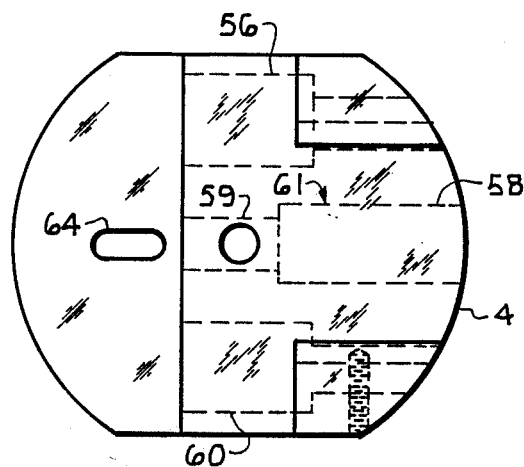
FIGS. 9A–E show the top, side, bottom and end view of the gripper body assembly.
Figure 9E:
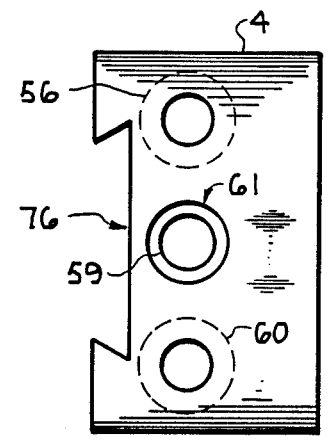
Figure 9B:
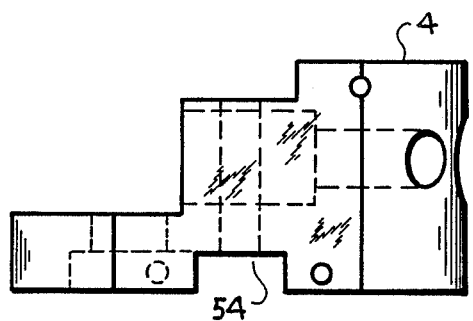
Figure 9D:
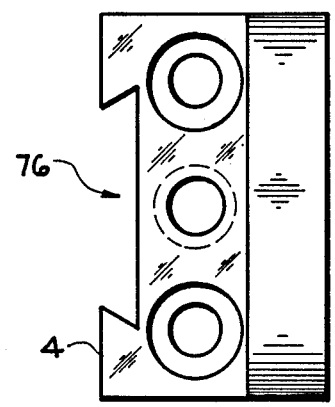
Figure 9C:
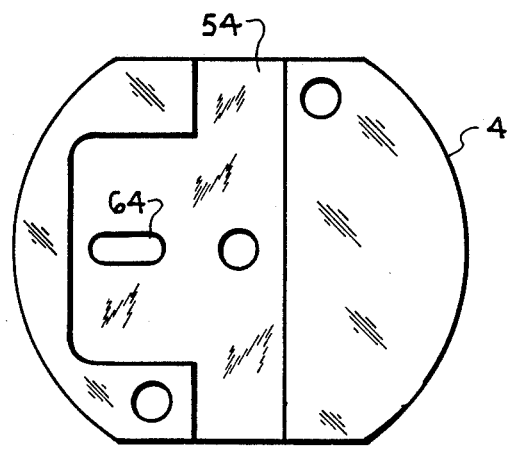

FIG. 10 shows a top view of the gripper assembly illustrating the operation of the cam 24. The cam 24 is inserted into the gripper body at cavity 54. The pin 52 perpendicular to the spring shaft 36 slides along the surface 27 of the cam. It is important that surface 27 of the cam 24 be ground flat so as to minimize frictional losses involved in transferring the linear force of the cam to the motion of the slidable jaw. In operation, when cam 24 is pressed into the gripper body in the X direction as shown, the protruding portion 25 forces pin 52 connected to the slidable jaw assembly 9 to move perpendicular in the Y direction. The pin 52 is constrained to move in the Y direction by slot 64 in the gripper body. The spring 48 provides a compression force urging the slidable jaw assembly 9 towards the fixed jaw 8. Upon releasing cam 24, spring 48 forces pin 52 in a direction opposite Y, pushing cam 24 out and urging slidable jaw 8 towards stationary jaw 6. Thus, pressing upon cam 24 and opening the jaws a part is inserted between the two jaws, the cam is then released and the force exerted by spring 48 firmly grips the part between the jaws and retains the part firmly in place.

Thus, a gripper useful in holding parts along a center axis aligned with a part manipulator has been shown. The gripper includes a combination spring mechanism and cam assembly causing a slidable jaw open when a cam is depressed and closed when the cam is released. The spring mechanism provides enough force for holding a part firmly between the jaws. A part manipulator with arms grabs the gripper and a ball plunger centers the gripper along the center axis of the part manipulator.

It will of course be understood that various changes may be made in form, details, arrangements and proportion of the parts without departing from the scope of the invention, herein, which generally stated, consists an apparatus capable of carrying out the objects above setforth, in the parts and combination of parts disclosed and defined in the appended claims.

What is claimed is:

1. A gripper for capturing a workpiece between co-operating opposed jaw members comprising:
    a base member;
    a first jaw member fixedly attached to said base member;
    a second jaw member slidably attached to said base member and oriented for sliding motion toward and away from said first jaw member;
    spring means for urging said second jaw member toward said first jaw member;
    a cam member slidably attached to said base member for motion transverse to a direction of motion of said second jaw member;
    means attached to said second jaw member and positioned for contacting said cam member, movement of said cam member effecting a movement of said second jaw member in a direction perpendicular to the direction of movement of said cam member;
    guide means fixedly attached to said second jaw member and slidably attached to said base member for maintaining a desired orientation of said second jaw member with said first jaw member;
    an attachment member connected to said base member and terminating in a pair of oppositely directed flanges, a conical depression formed in said attachment member substantially centrally of said flanges, said depression being adapted for receiving a ball plunger for exactly centering the gripper with respect to the plunger; and
    means cooperating with said flanges for forcing said gripper to center on the plunger.

2. The gripper of claim 1 and including an end plate attached to an external surface of said base member, said end plate extending parallel to a direction of extension of said first and second jaw members and being oriented such that a workpiece captured on two sides by the opposed jaw members can be positioned with a third side adjacent said end plate, and a set screw extending through said end plate for contacting and adjustably centering the workpiece.

3. A gripper assembly forming a transportable fixture for holding a workpiece in a predetermined orientation with respect to the assembly and being removably attachable to a manipulator for positioning the assembly and workpiece into an X-ray inspection station, the gripper assembly comprising:
    a body member being oriented in a horizontal plane and having an upper and lower surface;
    a stationary jaw member attached to said body member and extending from the upper surface thereof;
    a slidable jaw member coupled to the upper surface of said body member in opposed relationship to said stationary jaw member for capturing a workpiece therebetween;
    a pin member fixedly attached to said slidable jaw member and extending vertically downward through a slot in said body member, the slot being oriented to permit motion of said pin member in a horizontal direction to and fro with respect to said stationary jaw member;
    a spring actuator attached to said slidable jaw member, said actuator comprising a spring shaft extending horizontally through an aperture in said body member along a direction of motion said slidable jaw member, one end of said shaft being attached to said slidable jw member, and a spring mounted on said shaft for compression between a part of said shaft and said body member;
    cam means slidably coupled to said body member for motion in a horizontal plane and transverse to motion of said pin member, said cam means including a protruding cam surface positioned to contact said pin member for forcing said pin member to move away from said stationary jaw member when said cam means is forced toward said body member, said spring actuator forcing said slidable jaw member to close toward said stationary jaw member when said cam means is released;
    first and second alignment shafts attached to said slidable jaw member and extending horizontally through corresponding appertures in said body member along a direction of motion of said jaw member;
    linear bearing members coupled to each of said alignment shafts for slidably coupling said shafts to said body member; and
    support means attached to the lower surface of said body member, said support means including a downwardly extending portion terminating in horizontally extending flanges and having a centrally positioned conically shaped depression, wherein a manipulator having opposed pairs of inwardly extending arms adapted for engaging said flanges and having a vertically operable ball-shaped plunger for mating with said depression can automatically engage the gripper assembly and simultaneously center the assembly along an axis of motion of the plunger.

* * * * *